United States Patent
Zierhofer

(10) Patent No.: US 7,873,420 B2
(45) Date of Patent: Jan. 18, 2011

(54) PASSWORD PROTECTION FOR COCHLEAR IMPLANT

(75) Inventor: Clemens M. Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 266 days.

(21) Appl. No.: 11/761,614

(22) Filed: Jun. 12, 2007

(65) Prior Publication Data

US 2008/0009919 A1 Jan. 10, 2008

Related U.S. Application Data

(60) Provisional application No. 60/813,094, filed on Jun. 13, 2006.

(51) Int. Cl.
 *H04R 25/00* (2006.01)
(52) U.S. Cl. .......................... 607/57; 607/59
(58) Field of Classification Search ............ 607/31, 607/60, 32, 45, 54, 56, 57; 623/24; 128/419, 128/421, 422
See application file for complete search history.

(56) References Cited

U.S. PATENT DOCUMENTS 4,532,930 A * 8/1985 Crosby et al. ............... 607/57
6,493,587 B1 * 12/2002 Eckmiller et al. ............ 607/31
6,880,085 B1   4/2005 Balczewski et al. ......... 713/182
7,502,653 B2 *  3/2009 Daly ........................... 607/57
2007/0005118 A1 * 1/2007 Carter et al. ................. 607/57
2007/0260292 A1 11/2007 Faltys et al. .................. 607/57

OTHER PUBLICATIONS

Wilson, et al., "Better speech recognition with cochlear implants," *Nature*, vol. 352, pp. 236-238, Jul. 1991.
"Better speech recognition with cochlear implants," *Nature*, vol. 352, pp. 236-238, Jul. 1991.

* cited by examiner

*Primary Examiner*—Carl H Layno
*Assistant Examiner*—Paula J Stice
(74) *Attorney, Agent, or Firm*—Sunstein Kann Murphy & Timbers LLP

(57) ABSTRACT

An implant system includes an external portion adapted for placement external to a user, and an implantable portion adapted for placement internal the user. One of the internal portion and the external portion includes a first password for transmitting to the other one of the internal portion and the external portion. The other one of the internal portion and the external portion includes a second password. A match between the first password and the second password causes a first mode of operation.

6 Claims, 2 Drawing Sheets

PASSWORD PROTECTION FOR COCHLEAR IMPLANT

CROSS REFERENCE TO RELATED APPLICATIONS

This application claims priority from U.S. provisional patent application Ser. No. 60/813,094 filed Jun. 13, 2006, entitled "Password Protection for Cochlear Implant," which is hereby incorporated herein by reference, in its entirety.

TECHNICAL FIELD

The present invention relates to implants, and more particularly, to password protection for an implant such as a cochlear implant.

BACKGROUND ART

Cochlear implants and other inner ear prostheses are one option to help profoundly deaf or severely hearing impaired persons. Unlike conventional hearing aids that just apply an amplified and modified sound signal, a cochlear implant is based on direct electrical stimulation of the acoustic nerve. Typically, a cochlear implant stimulates neural structures in the inner ear electrically in such a way that hearing impressions most similar to normal hearing are obtained.

More particularly, a normal ear transmits sounds as shown in FIG. 1 through the outer ear 101 to the eardrum 102, which moves the bones of the middle ear 103, which in turn excites the cochlea 104. The cochlea 104 includes an upper channel known as the scala vestibuli 105 and a lower channel known as the scala tympani 106, which are connected by the cochlear duct 107. In response to received sounds transmitted by the middle ear 103, the fluid filled scala vestibuli 105 and scala tympani 106 function as a transducer to transmit waves to generate electric pulses that are transmitted to the cochlear nerve 113, and ultimately to the brain.

Some persons have partial or full loss of normal sensorineural hearing. Cochlear implant systems have been developed to overcome this by directly stimulating the user's cochlea 104. A typical cochlear prosthesis essentially includes two parts: the speech processor and the implanted stimulator 108. The speech processor (not shown in FIG. 1) typically includes a microphone, a power supply (batteries) for the overall system and a processor that is used to perform signal processing of the acoustic signal to extract the stimulation parameters. In state-of-the art prostheses, the speech processor is a behind-the-ear (BTE-) device. The implanted stimulator generates the stimulation patterns and conducts them to the nerve tissue by means of an electrode array 110 which usually is positioned in the scala tympani in the inner ear. The connection between speech processor and stimulator is usually established by means of a radio frequency (RF-) link. Note that via the RF-link both stimulation energy and stimulation information are conveyed. Typically, digital data transfer protocols employing bit rates of some hundreds of kBit/s are used.

One example of a standard stimulation strategy for cochlear implants is called "Continuous-Interleaved-Sampling strategy" (CIS), which was developed by B. Wilson (see, for example, Wilson B S, Finley C C, Lawson D T, Wolford R D, Eddington D K, Rabinowitz W M, "Better speech recognition with cochlear implants," Nature, vol. 352, 236-238, July 1991, incorporated herein by reference in its entirety).

A problem associated with a cochlear prosthesis that includes an external speech processor and an implanted stimulator is the possibility of interchanging an external speech processor of one cochlear implant with that of another. For example, this may occur with young cochlear implant users at school. Since the settings of the cochlear implants of two different users are typically different, various problems may arise in the cochlear implant and/or with the user(s).

SUMMARY OF THE INVENTION

In accordance with a first embodiment of the invention, an implant system includes an external portion adapted for placement external to the user, and an implantable portion adapted for placement internal the user. One of the internal portion and the external portion includes a first password for transmitting to the other one of the internal portion and the external portion. The other one of the internal portion and the external portion includes a second password. A match between the first password and the second password causes a first mode of operation.

In accordance with related embodiments of the invention, the at least one of the internal portion and the external portion may include a memory device for storing the first password and/or the second password. A programmer device may be capable of interfacing with at least one of the internal portion and the external portion to initialize one of the first password and/or the second password. At least one of the internal portion and the external portion may include a user interface for entering the first password and/or the second password.

In accordance with further embodiments of the invention, the first mode permits functionality associated with at least one of the external portion and the internal portion. If the first password does not match the second password, the external portion and the internal portion may instead enter a second mode in which functionality is decreased. The implant may be a cochlear implant. The external portion may include a first coil and the internal portion may include a second coil, the first coil adapted to be electromagnetically coupled with the second coil to transfer at least one of power and data. The other one of the internal portion and the external portion may transmit the first password to the other one of the internal portion and the external portion via the first and second coils.

In accordance with another embodiment of the invention, a method of using an implant system is presented. The implant system includes an external portion and an internal portion. The external portion is adapted for placement external to the system, while the implantable portion is adapted for placement internal the user. The method includes transmitting a first password from one of the internal portion and the external portion to the other one of the internal portion and the external portion. The first password is compared with a second password at the other one of the internal portion and the external portion. A first mode of operation is entered if there is a match between the first password and the second password.

In accordance with related embodiments of the invention, the method further may include storing the first and/or second password in a memory device in at least one of the internal portion and the external portion. The method may further include interfacing with at least one of the internal portion and the external portion to initialize the first or second password. A user interface may be manipulated on at least one of the internal portion and the external portion to enter the first or second password.

In accordance with further embodiments of the invention, the first mode may permit functionality associated with at least one of the external portion and the internal portion. The method may further include entering a second mode with decreased functionality if the first password and the second password do not match. The implant may be a cochlear implant. The external portion may include a first coil, the internal portion may include a second coil, wherein the method includes electromagnetically coupling the first coil with the second coil to transfer at least one of power and data. The first password may be transmitted between the one of the internal portion and the external portion to the other one of the internal portion and the external portion via the first and second coils.

In accordance with another embodiment of the invention, an implant system includes an external portion adapted for placement external to the user, and an implantable portion adapted for placement internal the user. The system further includes means for transmitting a password from one of the internal portion and the external portion to the other one of the internal portion and the external portion so as to enter a first mode of operation; means for comparing the first password with a second password at the other one of the speech processor and the stimulation module; and means for entering a first mode of operation if there is a match between the first password and the second password.

In accordance with related embodiments of the invention, at least one of the internal portion and the external portion may include a memory device for storing the first and/or password. A programmer device may be capable of interfacing with at least one of the internal portion and the external portion to initialize the first and/or second password. At least one of the internal portion and the external portion may include a user interface for entering the first and/or second password, along with power and/or other data.

In accordance with further embodiments of the invention, the first mode may permit functionality associated with at least one of the external portion and the internal portion. The system may further include means for entering a second mode with decreased functionality if the first password and the second password do not match. The implant may be a cochlear implant. The external portion may include a first coil, the internal portion may includes a second coil, with the first coil adapted to be electromagnetically coupled with the second coil to transfer at least one of power and data. One of the internal portion and the external portion may transmit the first password to the other one of the internal portion and the external portion via the first and second coils.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments of the invention, an implant system, such as cochlear implant system, includes an external portion and an internal portion. A password is transmitted between the external portion and the internal portion, which if verified places the implant in a first mode of operation. Details are discussed below.

Figure 1:
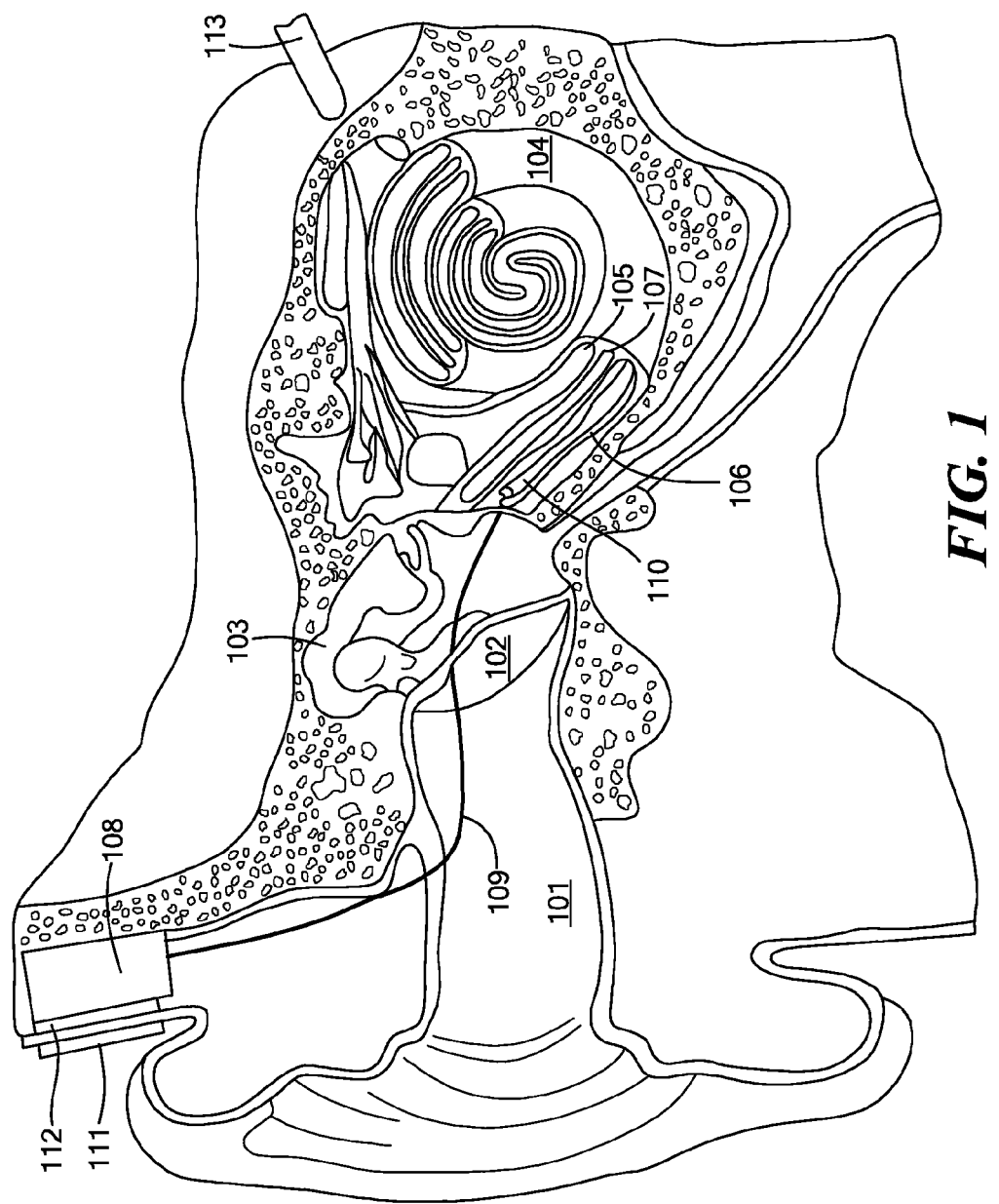
FIG. 1 shows the ear structure of a human ear and a typical cochlear implant system.
Figure 2:
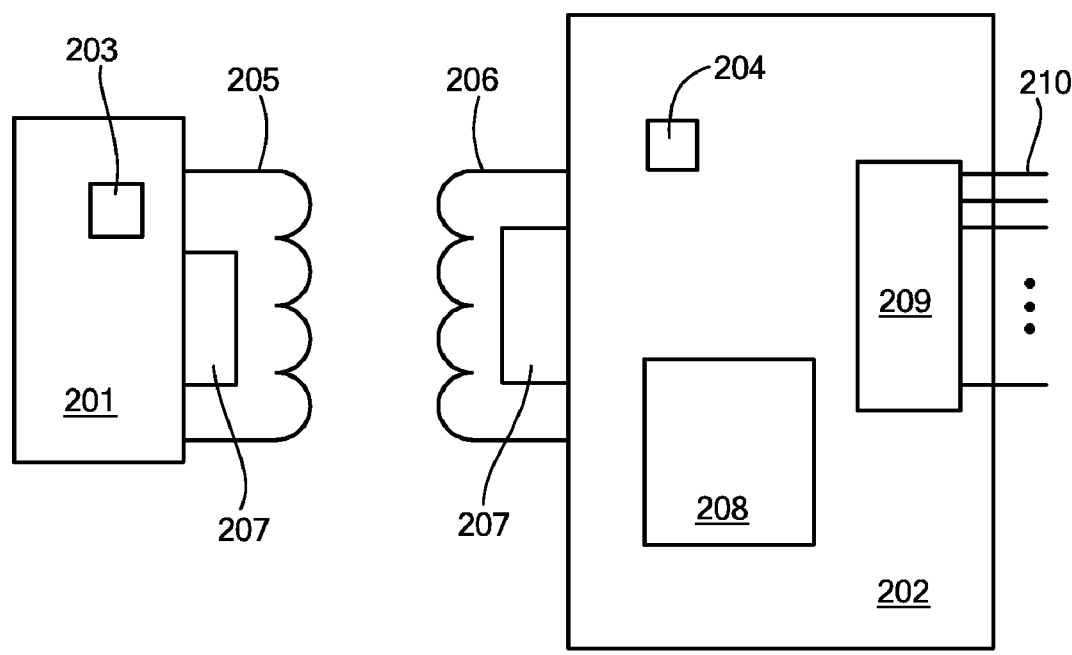
FIG. 2 is a block diagram of a cochlear implant system with password protection, in accordance with an embodiment of the invention.

FIG. 2 is a block diagram of a cochlear implant system that includes password protection, in accordance with an embodiment of the invention. The cochlear system includes an external portion 201, which may be for example, a speech processor 201 as described above. The speech processor 201 may include, without limitation, a power supply and an RF transmitter/coil 205. An implanted signal processor and/or stimulator 202 (for clarity, hereinafter stimulator 202), also described above, may receive power and/or modulated data transmitted by the transmitter coil 205 to receiver coil 206. Magnets 207 may aid in positioning coils 205 and 206 adjacent each other. In various embodiments, the external portion 201 may communicate with a fully implantable cochlear implant.

In exemplary embodiments, the speech processor 201 may include a first password 204, and the stimulator 202 may include a second password 203. The passwords may be stored for example, in a memory device, such as a ROM or programmable memory. A programming device (not shown) may be used to interfacing with the speech processor 201 and/or the stimulator 202 so as to initialize the associated passwords. In various embodiments, the speech processor 201 and/or the stimulator may includes a user interface, such as a dip switch or thumbwheel, for entering their associated passwords. In still other embodiments, the passwords may be set in the factory, and may not be capable of being changed thereafter.

Upon a triggering event, such as, without limitation, turning on the speech processor 201 and/or placing the speech processor 201 adjacent the stimulator 202, the speech processor 201 transmits the first password to the stimulator 202 via coils 207 and 208. Upon verifying that the first password matches the second password, the stimulator 202 may then enter a first mode of operation. It is to be understood that instead of the first password being transmitted to the stimulator 202, the second password may be transmitted to the speech processor 201 instead, with the verification occurring in the speech processor 201.

The first mode may be an operational mode between the speech processor 201 and the stimulator 202 that permits, without limitation, full or partial cochlear implant functionality. If it is determined that the first and second passwords do not match, the cochlear implant may enter a second mode where, for example, various functionality is not allowed and/or decreased. The speech processor 201 may provide an alert to the cochlear implant user if the passwords do not match. The alert may occur at the speech processor 201. Such an alert may be a visual alert (e.g., a light blinking), an audio alert, and/or a vibration. Alternatively, or in combination with the alert at the speech processor 201, the implanted stimulator 202 may stimulate the cochlea so as to provide an alert perceived by the user.

More than one password may be used in the system. Each password may permit differing functionality. For example, upon successful verification of a first password, operational functionality may be permitted such that the user's cochlea is properly stimulated. Alternatively, if a second password is transmitted and verified, a diagnostic, data accessing and/or programming mode may, without limitation, be enabled. Diagnostics/data provided may check, without limitation, that the implant is functioning correctly, battery life and/or provide a serial number. The programming mode may provide various parameters, such as an amplification level.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, linker, or locator.) Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web.)

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL.)

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant system, the system comprising:
a speech processor for converting an incoming acoustic signal into an encoded signal, the speech processor adapted for placement external to a user;
a stimulation module for stimulating an electrode array as a function of the encoded signal received from the speech processor, the stimulation module adapted for placement internal the user; and
wherein one of the stimulation module and the speech processor includes a first password preprogrammed in non-volatile memory for transmitting to the other one of the stimulation module and the speech processor, the other one of the stimulation module and the speech processor including a second password preprogrammed in non-volatile memory, wherein a match between the first password and the second password causes a first mode of operation in which the electrode array is stimulated as a function of the encoded signal, and wherein a mismatch between the first password and the second password causes a second mode of operation that prevents the electrode array from being stimulated as a function of the encoded signal, such that the speech processor is not interchangeable between stimulation modules with different passwords.

2. The implant system according to claim 1, wherein the speech processor is coupled to a first coil, the stimulation module is coupled to a second coil, and the first coil is adapted to be electromagnetically coupled with the second coil to transfer at least one of power, the encoded signal, and the first password.

3. A method of controlling a cochlear implant system, the implant system including a speech processor adapted for placement external to the system, the speech processor for converting an incoming acoustic signal into an encoded signal, the implant system further including a stimulation module adapted for placement internal the user, the stimulation module for stimulating an array of electrodes as a function of the encoded signal received from the speech processor, the method comprising:
transmitting a first password from one of the speech processor and the stimulation module to the other one of the speech processor and the stimulation module, the first password preprogrammed in non-volatile memory in the one of the speech processor and the stimulation module;
comparing the first password with a second password at the other one of the speech processor and the stimulation module, the second password preprogrammed in non-volatile memory in the other one of the speech processor and the stimulation module; and
entering a first mode of operation if there is a match between the first password and the second password, such that the electrode array is stimulated as a function of the encoded signal, and wherein a mismatch between the first password and the second password causes a second mode of operation so as to prevent the electrode array from being stimulated as a function of the encoded signal, such that the speech processor is not interchangeable between stimulation modules with different passwords.

4. The method according to claim 3, wherein the speech processor is attached to a first coil, wherein the stimulation module includes a second coil, and wherein the method includes electromagnetically coupling the first coil with the second coil to transfer power, data and the first password.

5. A cochlear implant system, the system comprising:
an external portion adapted for placement external to the user, the external portion includes means for converting an incoming acoustic signal into an encoded signal;
an implantable portion adapted for placement internal the user, the implantable portion includes means for stimulating an electrode array as a function of the encoded signal;
means for transmitting a first password from one of the external portion and the implantable portion to the other one of the external portion and the implantable portion, the first password preprogrammed in non-volatile memory in the one of the external portion and the implantable portion;

means for comparing the first password with a second password at the other one of the external portion and the implantable portion, the second password preprogrammed in non-volatile memory in the other one of the external portion and the implantable portion; and means for entering a first mode of operation if there is a match between the first password and the second password, such that the electrode array is stimulated as a function of the encoded signal, and wherein a mismatch between the first password and the second password causes a second mode of operation that prevents the electrode array from being stimulated as a function of the encoded signal, such that the external portion is not interchangeable between implantable portions with different passwords.

6. The implant system according to claim 5, wherein the external portion is coupled to a first coil, the implantable portion is coupled to a second coil, and the first coil is adapted to be electromagnetically coupled with the second coil to transfer power, data, and the first password.

* * * * *